(12) United States Patent
Mackenzie et al.

(10) Patent No.: US 7,040,146 B2
(45) Date of Patent: May 9, 2006

(54) SOIL OR SNOW PROBE (75) Inventors: Roderick Mackenzie, Malvern (AU); Warwick Payten, Banksia (AU)

(73) Assignee: Himachal Safety Systems Pty Ltd, Victoria (AU)

( * ) Notice: Subject to any disclaimer, the term of this patent is extended or adjusted under 35 U.S.C. 154(b) by 0 days.

(21) Appl. No.: 10/498,547

(22) PCT Filed: Dec. 23, 2002

(86) PCT No.: PCT/AU02/01760

§ 371 (c)(1),
(2), (4) Date: Jun. 14, 2004

(87) PCT Pub. No.: WO03/056302

PCT Pub. Date: Jul. 10, 2003

(65) Prior Publication Data

US 2005/0076709 A1    Apr. 14, 2005

(30) Foreign Application Priority Data

Dec. 28, 2001  (AU) .................................. PR9771

(51) Int. Cl.
*G01N 3/00* (2006.01)
*G01N 3/32* (2006.01)
*G01N 3/42* (2006.01)

(52) U.S. Cl. .................... 73/81; 73/82; 73/83; 73/85

(58) Field of Classification Search ............... 73/81, 73/82, 84, 85, 862.636, 862.68, 12.09, 12.11, 73/12.13
See application file for complete search history.

(56) References Cited

U.S. PATENT DOCUMENTS

| 4,382,384 A | * | 5/1983 | Mitchell et al. ............... 73/594 |
| 4,492,111 A | * | 1/1985 | Kirkland ......................... 73/84 |
| 4,644,805 A |   | 2/1987 | Hafner ...................... 73/862.68 |
| 5,831,161 A | * | 11/1998 | Johnson et al. ............ 73/432.1 |

FOREIGN PATENT DOCUMENTS

| DE | 3834846 A | 4/1990 |
| FR | 2817344 A | 5/2002 |
| WO | FR 2250433 A | 5/1975 |
| WO | WO 92/15000 A | 9/1992 |

\* cited by examiner

*Primary Examiner*—Hezron Williams
*Assistant Examiner*—Tamiko Bellamy
(74) *Attorney, Agent, or Firm*—Connolly Bove Lodge & Hutz LLP (57) ABSTRACT

A soil or snow probe which incorporates a load cell in the probe head and also an accelerometer so that a vertical strength profile of the snow or soil can be established. The device does not need to be driven at a constant speed and can be manually driven into the soil or snow. The resistance to penetration is measured using a load cell which incorporates a low duro polymer selected for its ability to behave like a non compressible fluid. The device is portable and provides data quickly.

9 Claims, 9 Drawing Sheets

SOIL OR SNOW PROBE

FIELD OF THE INVENTION

This invention relates to probes for measuring density and strength characteristics of soil or snow.

BACKGROUND TO THE INVENTION

Soil or snow strength characteristics in vertical plane are important in determining load bearing capacity and in snow characterisations of the snow layers is important in predicting the likelihood of avalanches.

U.S. Pat. No. 4,806,153 discloses a soil penetrometer incorporating sensors to measure penetration resistance and pore water pressure and a recording and control unit to store the sensor readings for transfer to an above ground computer for analysis.

U.S. Pat. No. 6,062,090 discloses a method and penetrometer for measuring as a function of time the resistance to penetration of a soil bed for evaluating highway and railroad bed surfaces.

Since the middle of the century there have been several hundred documented fatal avalanche accidents claiming hundreds of lives. Recent years have seen an increase in the occurrence of fatalities. Over 80% of the fatalities are climbers, back country skiers, out of bounds down hill skiers and snowmobiles.

U.S. Pat. No. 5,831,161 discloses a snow penetrometer in which the penetrating head is mounted on a tripod and driven at constant speed. A force transducer measures the resistance so that a resistance profile through a vertical section can be obtained.

U.S. Pat. No. 5,864,059 discloses a probe for measuring snow depth that uses a floating plate that slides on the shaft and a magnetorestrictive transducer filament senses the travel of the shaft.

The commonly used method for predicting avalanches is to dig a trench (called a snow pit) to assess snow pack stability from the stiffness and temperature in the snow wall. This takes about 35 minutes and does not provide a cross-slope profile of a slope unless several snow pits are dug. The snow penetrometers discussed above do not provide a measure that can be used to predict the likelihood of an avalanche.

It is an object of this invention to provide a probe that can provide a vertical profile of soil or snow strength parameters and other soil or snow condition parameters such as water content or temperature and present this data to assist in assessing stability.

SUMMARY OF THE INVENTION

To this end the present invention provides a penetrating probe for testing soil or snow stability which includes
  a) a head shaped for penetrating soil or snow
  b) a sensing unit mounted in said head to sense the resistance to penetration which includes a load cell incorporating a low duro polymer wherein the impact of the head impacting the soil or snow is transferred to the low duro polymer
  c) an accelerometer to sense the acceleration of the head as it moves
  d) a processor able to receive signals from said sensing unit and programmed to analyse the data and present it as a vertical profile of penetration resistance with depth of penetration.

By positioning the sensor unit in the head and not at the end of the shaft as proposed in U.S. Pat. No. 5,831,161 noise from the vibration of the drive shaft is eliminated and makes interpretation of the sensor signals easier.

An important advantage derived from the use of the accelerometer is the ability to manually insert the probe into soil or snow. The manual insertion results in acceleration and velocity changes from which the distance travelled can be calculated knowing the time taken. The distance traveled gives the depth of snow and by correlating the resistance to penetration with time the resistance at different depths can be calculated and graphed.

This invention is partly predicated on the discovery that using a low duro polymer in the load cell reduces the interference of external noise in the load cell signals.

In another aspect this invention provides a force sensor which includes
  a) a low duro polymer
  b) an impact head arranged to seat on said low duro polymer such that forces acting on said impact head are transmited to said low duro polymer
  c) a sensor in contact with said low duro polymer to provide a measure of the forces transmitted to said low duro polymer.

The low duro polymer preferably has a low shore hardness of 5 to 30 more preferably 8–10 and may be selected from rubber like materials preferably with linear compression gradients such as natural and synthetic rubbers, polyurethanes and preferably silicone polymers such as those sold by Dow Corning. It is preferred that the material has a low coefficient of thermal expansion, low shear strength, a high bulk modulus and remains flexible at low temperatures. The selected low duro polymers provide an hydraulic advantage with low hysteresis.

The load cell preferably consists of at least one strain gauge mounted to sense the variation in impact forces imparted to the low duro polymer. The low duro polymer is selected on its ability to behave as a non-compressible fluid. The load cell abuts the shaped impact portion of the head or a shaft on which the impact portion is mounted. The interface between the impact shaft and the load cell polymer is spherically domed. The shaped head is preferably domed.

This load cell of this invention does not suffer from noise in the signals due to the use of the low duro polymer and because of the combination of the polymer and the shape of the bearing area on the polymer the sensitivity is much greater than for sensors of comparable cost. Sensitivity is of the order of 0.1 grams in 40 kgms or 1:400,000.

The use of an accelerometer eliminates the need for the head to have a constant velocity and enables the head to be manually driven in the soil or snow and does away with the need for a constant velocity penetrometer which requires a tripod, a motor and a drive shaft. This saves component cost and improves the portability of the probe. The accelerometer may be part of the sensing unit or a separate unit in the head or may be at any point on the probe shaft to which the head is attached as long as its movement parallels the movement of the head.

Thus in another aspect the present invention provides a penetration probe which includes
  a) a head shaped for penetrating soil or snow
  b) a sensing unit mounted in said head to sense parameters of the soil or snow
  c) an accelerometer to sense the acceleration of the head as it moves d) a processor able to receive signals from said accelerometer and programmed to analyse the accelerometer data and present it as a measurement of depth of penetration e) said processor also receiving signals from said sensing unit and programmed to analyse the sensing signals as a function of depth of penetration.

The sensor unit may also incorporate sensors other than resistance to penetration sensors. For determining snow stability, a vertical temperature profile of the snow is an important guide to the likelihood of future metamorphism of the snow layers and the likelihood of an avalanche. Thus a temperature sensor capable of measuring the changes in temperature as the penetrometer moves through the snow is an important addition to a snow probe.

Another method of measuring snow properties is to measure snow density using a capacitor to measure changes in the capacitance which varies with the density of the snow.

Water content as measured by moisture levels or water pressure is an important guide to soil stability and its capacity to bear loads. A water sensor or water pressure sensor is therefor a desirable addition to the sensor unit when the probe is intended for soil testing.

For snow testing additional information can be gleaned from the penetration resistance data if multiple heads are used. An array of 3 heads equally spaced from the central shaft and of different diameters will provide 3 different resistance readings due to the different ratios of circumferences of the impact heads in relation to the bearing area. This enables vertical and or shear strength of the snow to be determined.

In another aspect this invention provides a method of assessing the stability of a snow slope which includes the steps of a) using a probe to produce a profile of resistance to penetration as a function of penetration depth b) repeating step a) at different points on the slope c) integrating the results of step b) to produce a profile of the slope This enables a slope to be assessed for avalanche risk in a very short time. Preferably the measurements are made at several points in line across a contour of the slope and several such lines down the slope are measured and analysed. Alternatively lines of points down the slope may be measured. The points are preferably 10 to 15 meters apart and the contour lines are 50 to 75 meters apart. The best sections of a slope to take points on are adjacent convex rolls as experience shows that these are more likely sites for avalanches.

BRIEF DESCRIPTION OF THE DRAWINGS

A preferred embodiment of this invention is a snow probe for testing the stability of snow slopes in order to assess the risk of avalanches.

DETAILED DESCRIPTION OF THE INVENTION

The snow probe equipment required for the present invention is a probe head containing the sensors attached to a collapsible shaft up to 5 meters in length with a portable control box containing the programmed controller and processor and a display screen or printer for displaying the output.

Figures 1, 2:
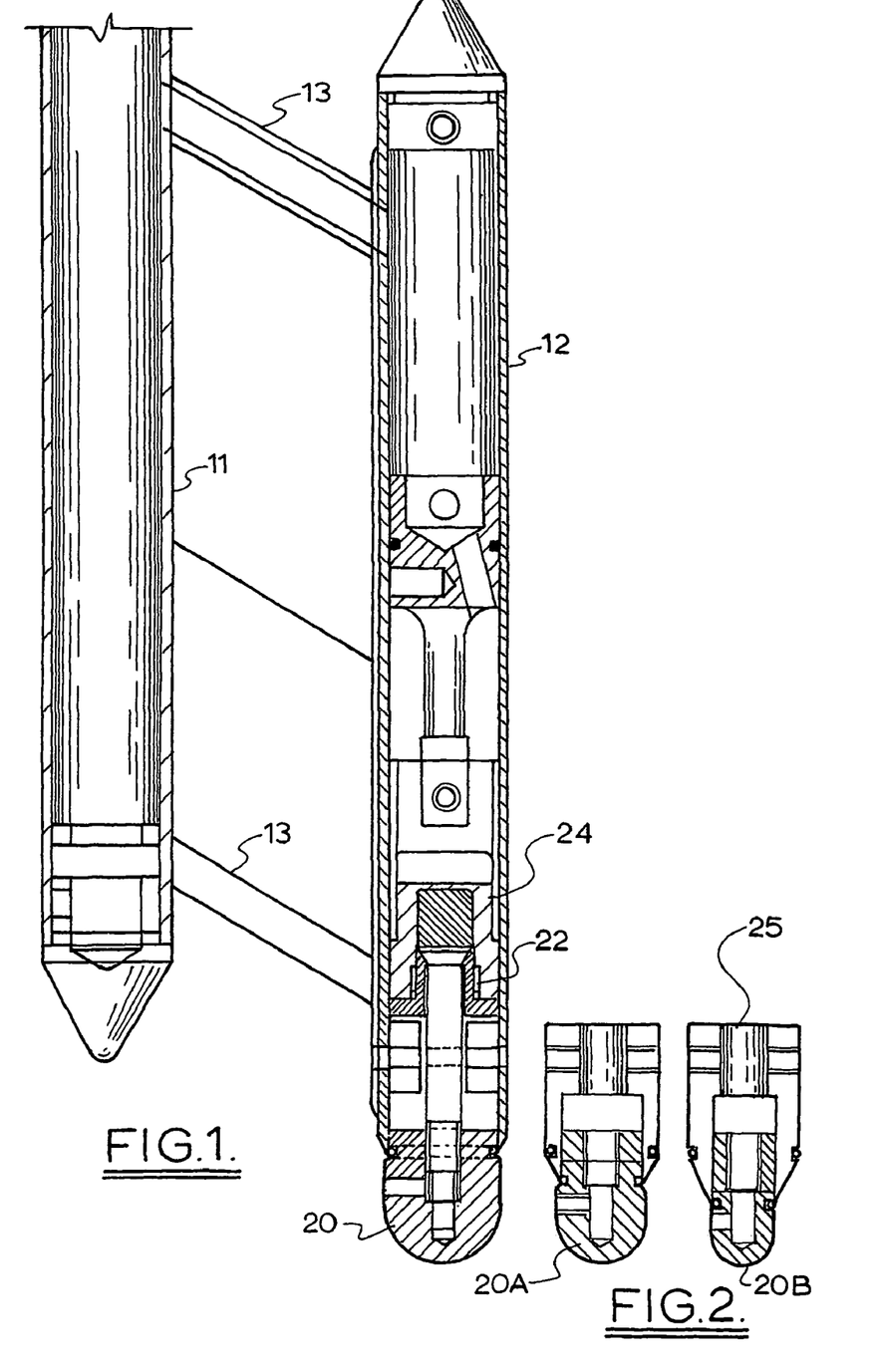
FIG. 1 illustrates a schematic view of the sensor head of this invention.
FIG. 2 shows a detail of the penetrating heads of the other two sensor tubes in the device of FIG. 1.
Figure 3:
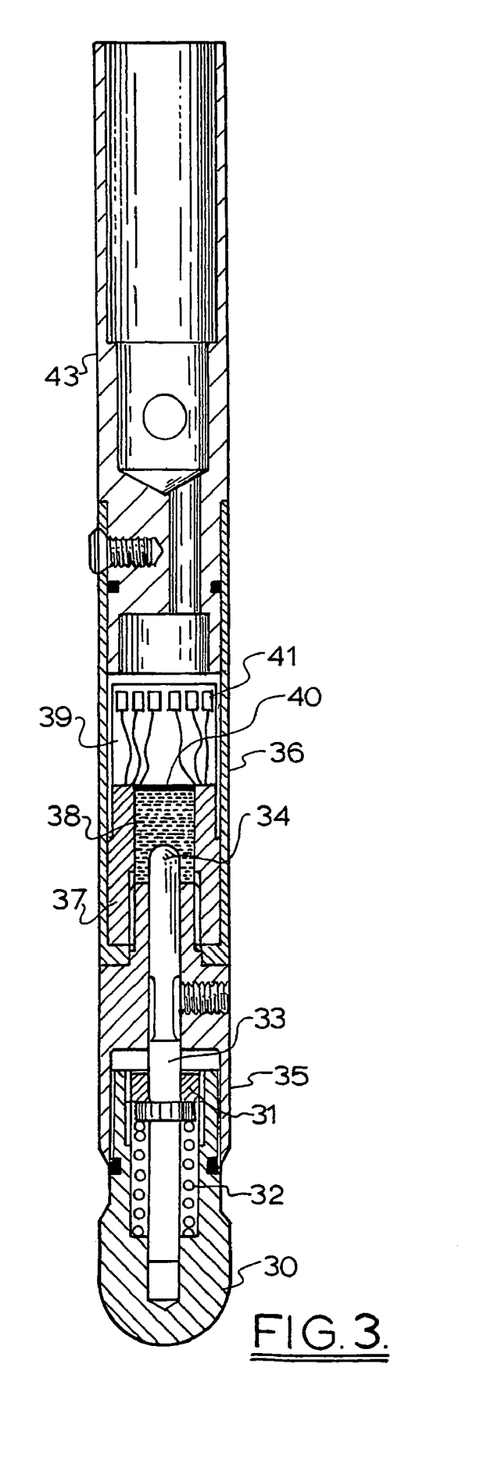
FIG. 3 is a schematic cross section of another version of a sensor tube according to this invention.
Figure 4:
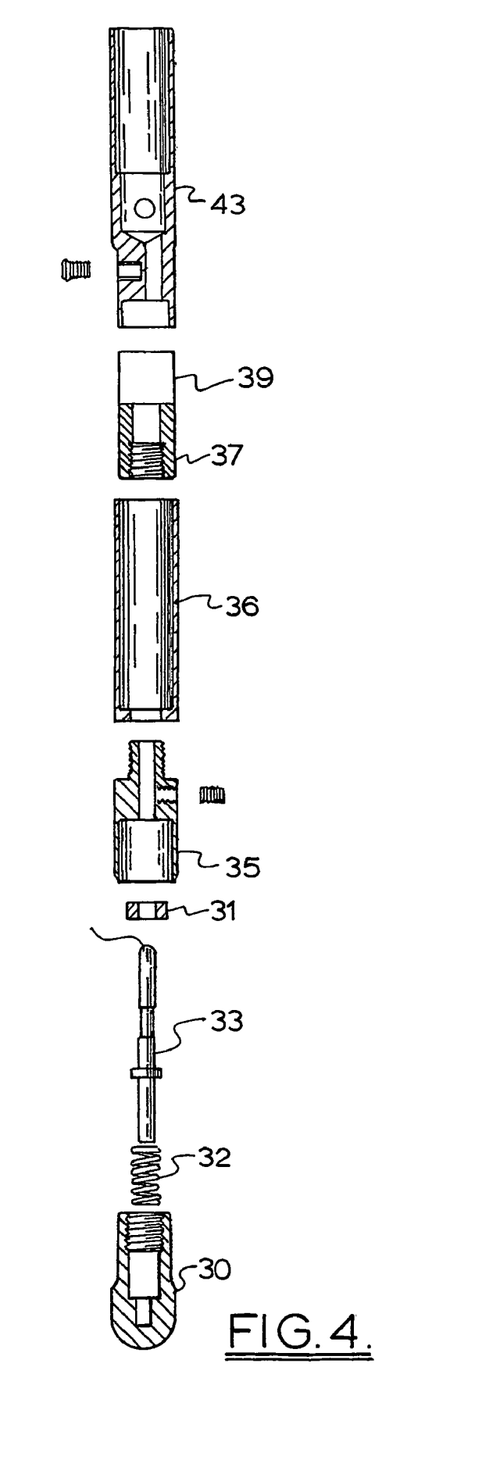
FIG. 4 is an exploded view of the sensor tube of FIG. 3.

As shown in FIG. 1 the probe has a central shaft 11 and 3 sensor tubes 12 equally spaced from each other and the central shaft 11.

The sensor tubes 12 are rigidly attached to the shaft 11 by way of the struts 13.

At the lower end of each sensor tube 12 is a penetrator head 20 which is of a predetermined diameter. Each of the 3 heads 20 is of varying diameter up to a diameter equal or greater to the diameter of the sensor tube 12. Each penetrator head, 20 in FIG. 1 and 20A and 20B in FIG. 2, is domed to present a shaped surface to provide an optimum resistance to penetration. Each penetrating head 20, 20A or 20B is mounted on a piston 22 that is mounted within the sensor tube 12. The piston 22 is seated on the low duro silicone polymer 25 of the load cell 24. The ratio of the sensing head area to the bearing area is about 1:8 which increases the signal about 20 times The load cell has a strain gauge attached to sense the pressure generated in the low duro polymer by the penetrator head passing through the snow. The low duro polymer is Silastic 3487 sold by Dow Corning with a hardness of Shore A 8–10. The strain guage is a Micro Measurements E A 06–228 JB of 350 ohm.

The second version of the sensor tube as illustrated in FIGS. 3,4 and 7–8 includes a penetrating tip 30. having a domed head. A sharper tip is shown in FIG. 5 where the tip 50 is shown in cross section with the cavity 51 to accommodate the shaft 33 and a wider cavity 52 to accommodate the spring 32.

Figures 5, 6, 7:
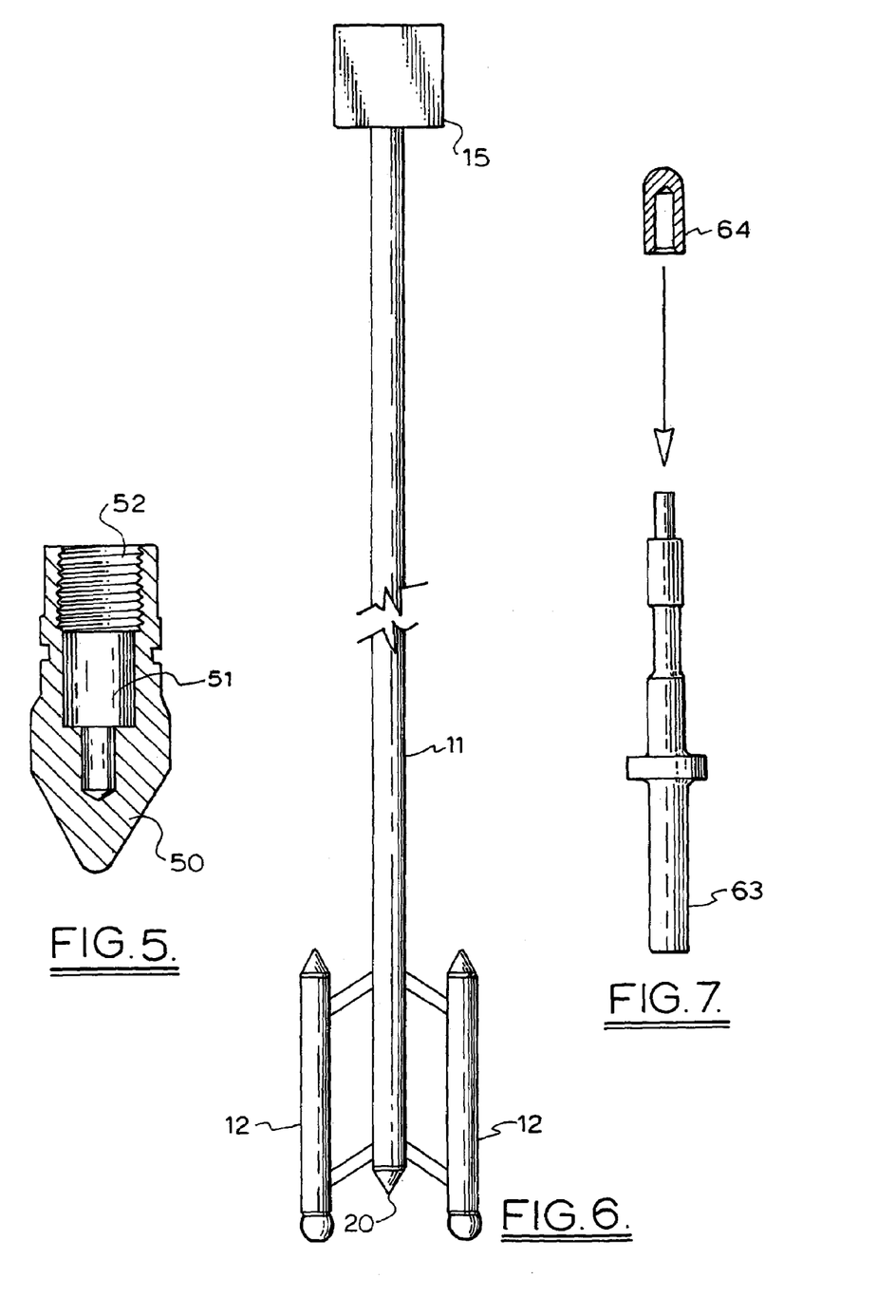
FIG. 5 is a schematic cross section of another version of the penetrating tip according to this invention.
FIG. 6 is a schematic view of the sensor probe shaft with the electronics module at one end and the penetrator heads at the other.
FIG. 7 is a cross sectional view of the shaft and load cell tip of the device shown in FIG. 3.
Figure 8:
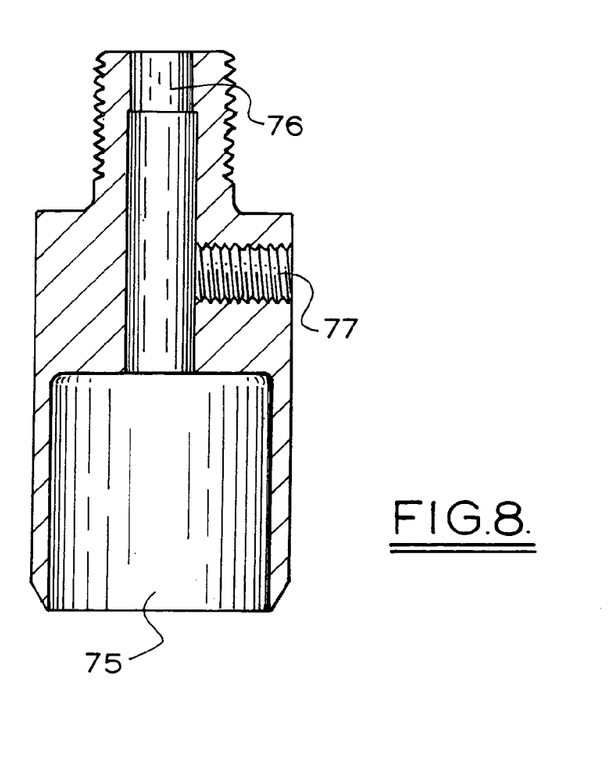
FIG. 8 is a view of the gland nut that fits about the shaft of FIG. 6.

The nut 31 slides down the top of the shaft 33 to abut the cylindrical flange 65 shown in FIG. 6.

Figure 9:
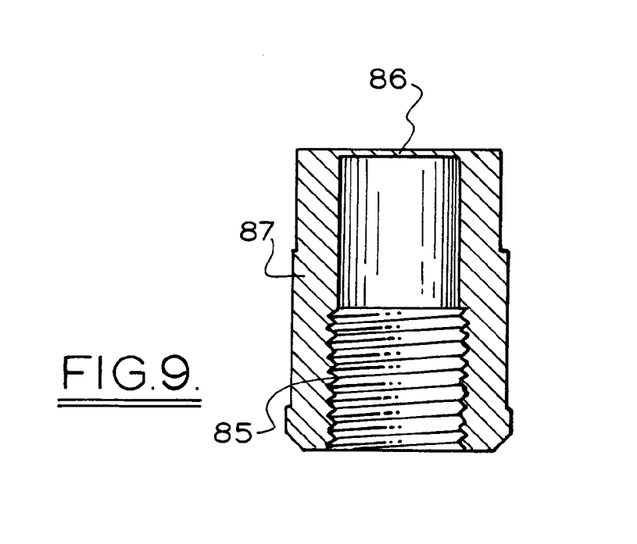
FIG. 9 is a cross sectional view of the load cell from the sensor tube of FIG. 3.

The body of the tip 30 fits within the gland nut 35 shown in more detail in FIG. 7. The shaft 33, 63 passes through the tube 76. A screw threaded lock can be inserted in the hole 77 to lock the shaft 33, 63 when the sensor tube is not in use. The transducer or load cell 37 seats about the top of the gland nut 35 so that the end 34 (FIG. 3) and 64 (FIG. 7) of the shaft 33 sits on the low duro polymer 38. The end of the gland nut 35, 75 seats in the widened portion 85 of the load cell 87 (FIG. 9). A strain guage 40 lies across the base of the polymer 38. The electronics circuitry 41 for the strain guage 40 (shown as 86 in FIG. 9) is housed in the housing 39. The housing 39 and the load cell 37 (87 in FIG. 9) are contained within tube 36. The tube 36 is attachable to the main shaft 43. The probe is protected from damage by overload, by the provision of shaft screws.

An accelerometer is located in the electronics and display module 15 mounted on the central probe shaft 11 as shown in FIG. 6. The accelerometer is preferably a solid state micro electromechanical sensor which generates an electrical signal based on the speed of change of its position. The preferred accelerometer is an ADXL 105 single axis with a range of +/−5 gm an analogue output ratiometric to supply 2 mg resolution, a 10 KHz bandwidth an on board temperature sensor, low power and voltage 0.2 mA at 5V operation down to 2.7 V.

The readings from the accelerometer are integrated twice to give depth measurements from the surface and is accurate to within a mm per meter.

During the push or insertion of the probe three primary signals are taken with a resolution of 500 readings per second. In snow these signals are acceleration, force and temperature. The process is as follows:

1. the acceleration is integrated to velocity and a check is made based on start and finish to ensure velocity is zero at both ends of the measured push.
2. data slope adjustments are performed to modify the signals which is then integrated again. Once the velocity is zeroed a final integration is performed to compute displacement
3. sampling is used during integration to ensure noise reduction in the signal;
4. the displacement is then related to the force reading which is also over sampled and averaged.
5. once the velocity of the push is calculated a look up table can be used based on the force and velocity to cancel out any inertial effects leading to incorrect force readings due to strain hardening of the snow pack.
6. the data is stored to flash memory
7. Frequency decimation and smoothing of the data is performed to allow display on a graphics screen with limited resolution and to allow pattern recognition
8. Frequency decimation ensures that all peaks and valleys are maintained during smoothing.
9. Approximately 8000 readings are decimated to around 120
10. A pattern recognition program is used to break up the readings into layers more commonly used by ski guides.

Figure 10:
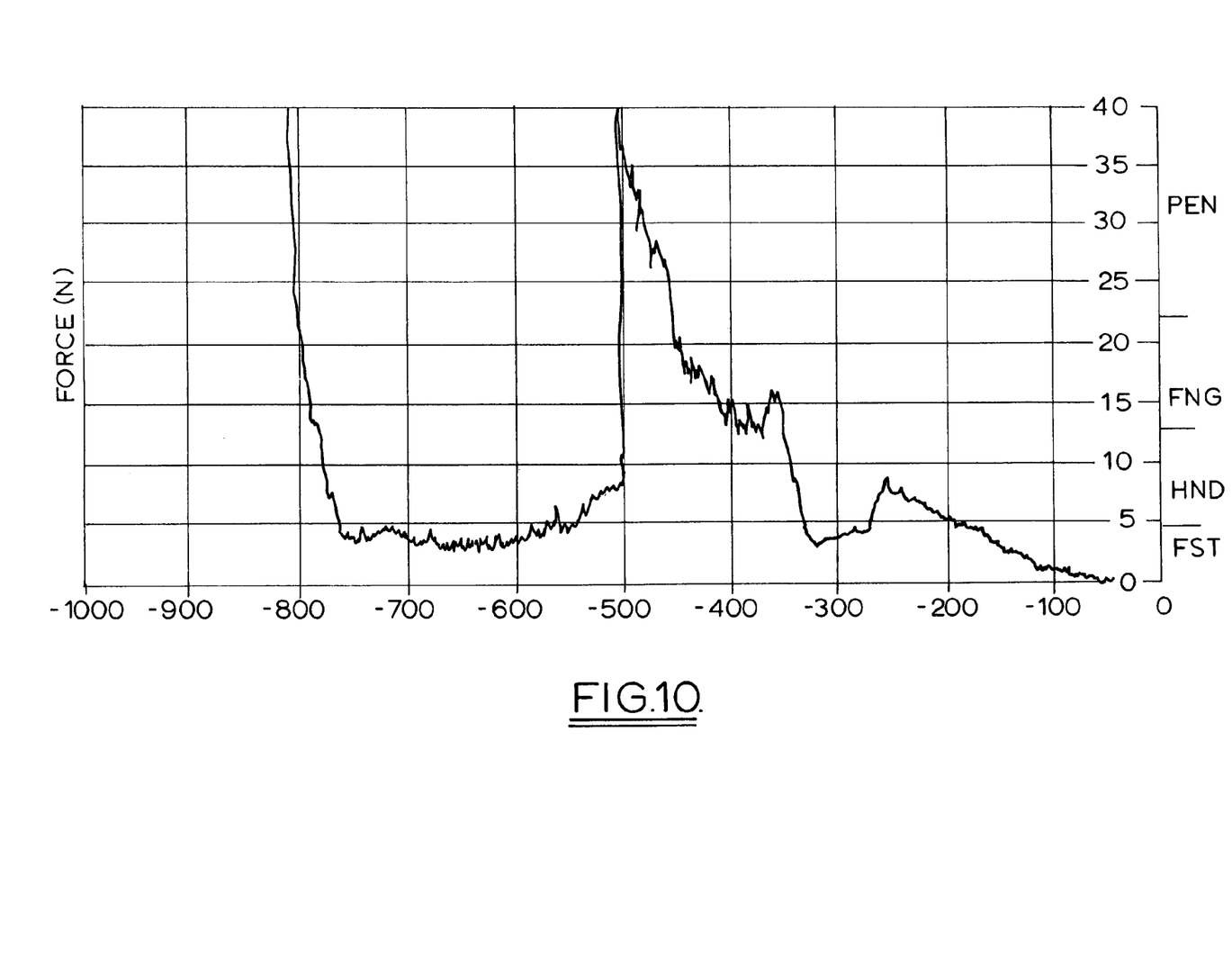
FIG. 10 illustrates data from a probe into a snow pack.

In FIG. 10 a single probe measurement shows the penetration resistance plotted against depth. The layer was about 800 mm deep and the plot shows a weakness at about 500 mm indicative of instability which can lead to an avalanche.

This data is down loaded onto a portable computer for analysis and presentation as a screen report.

Figure 11:
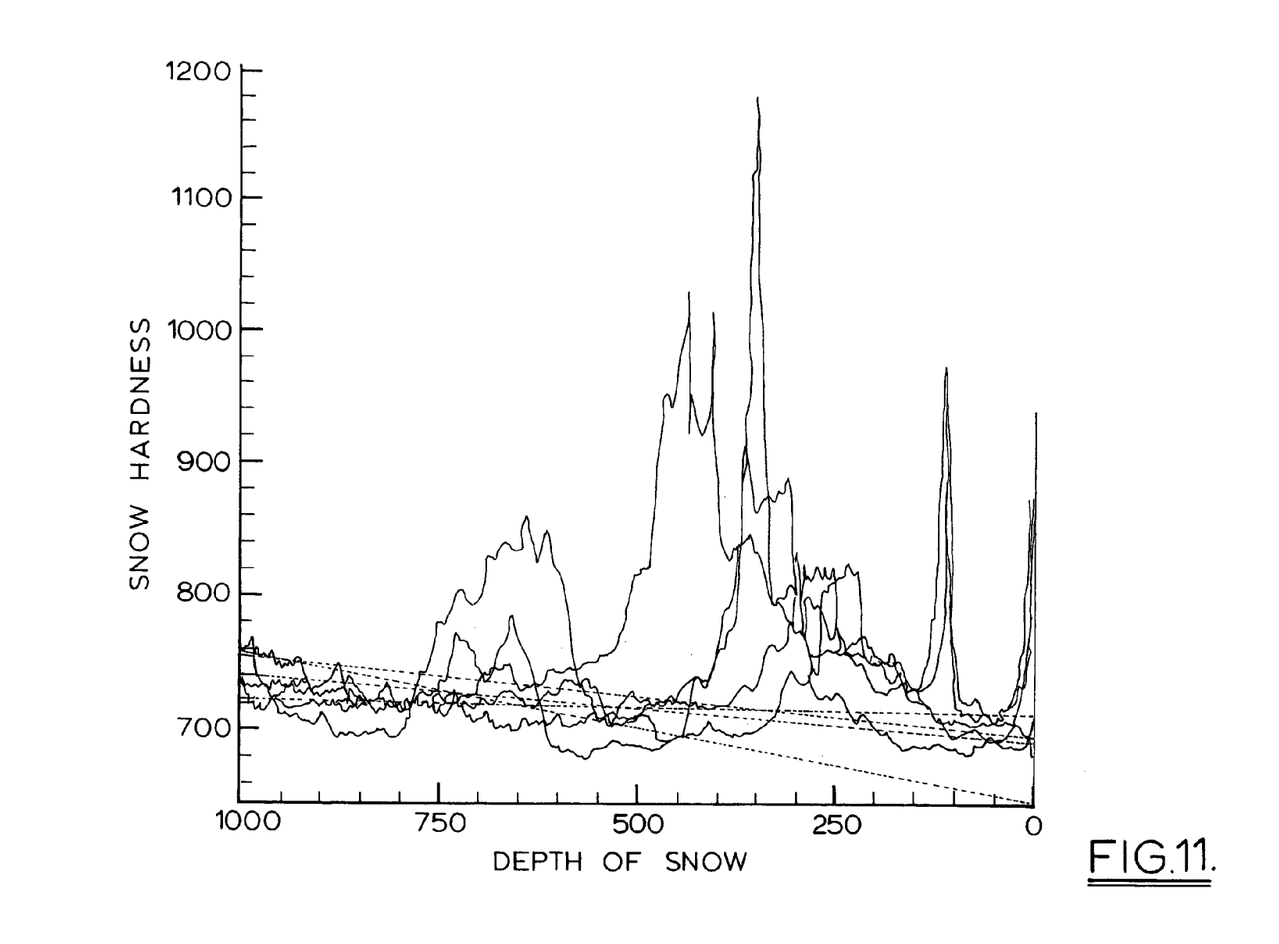
FIGS. 11 to 14 are plots of a multiple set of readings across a snow slope.
Figure 12:
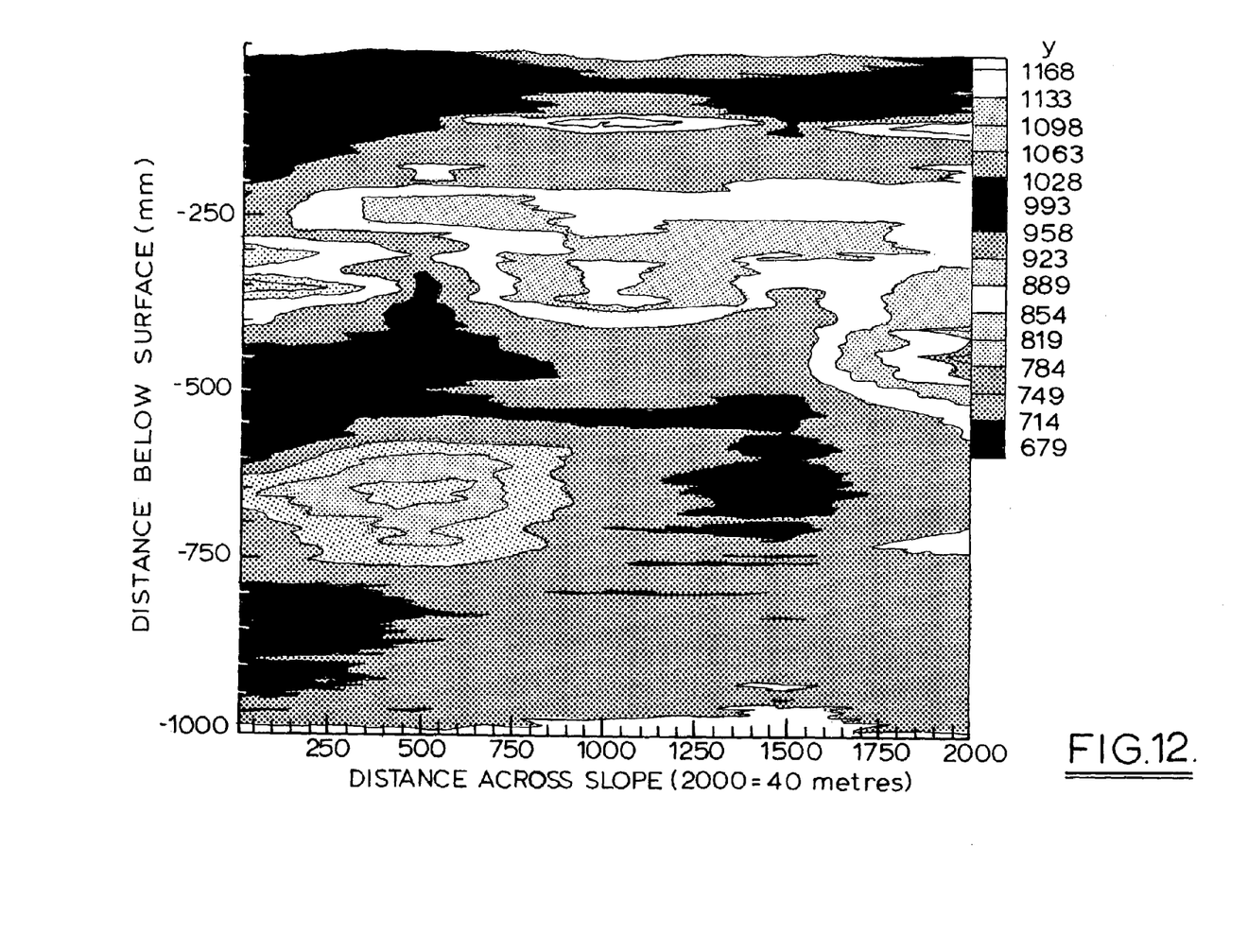
Figure 13:
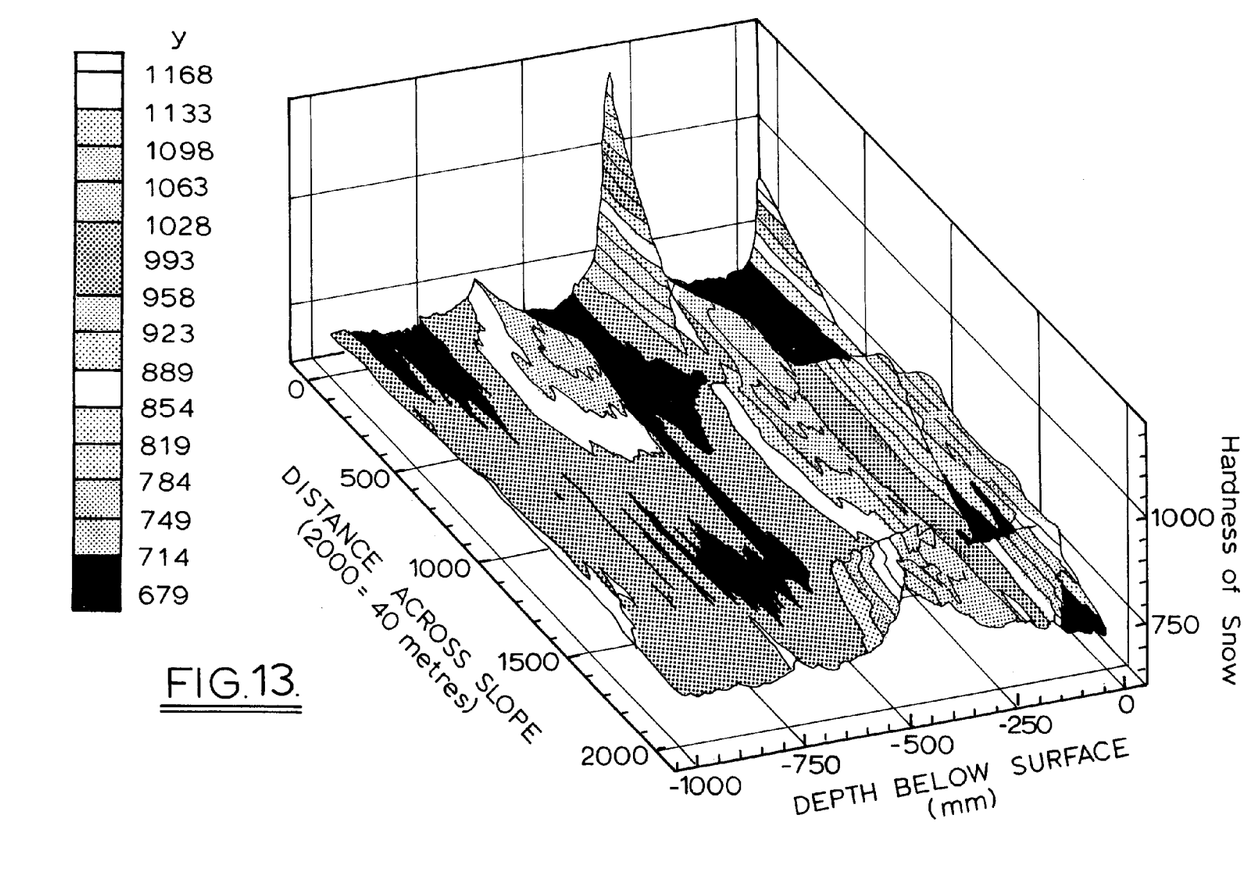
Figure 14:
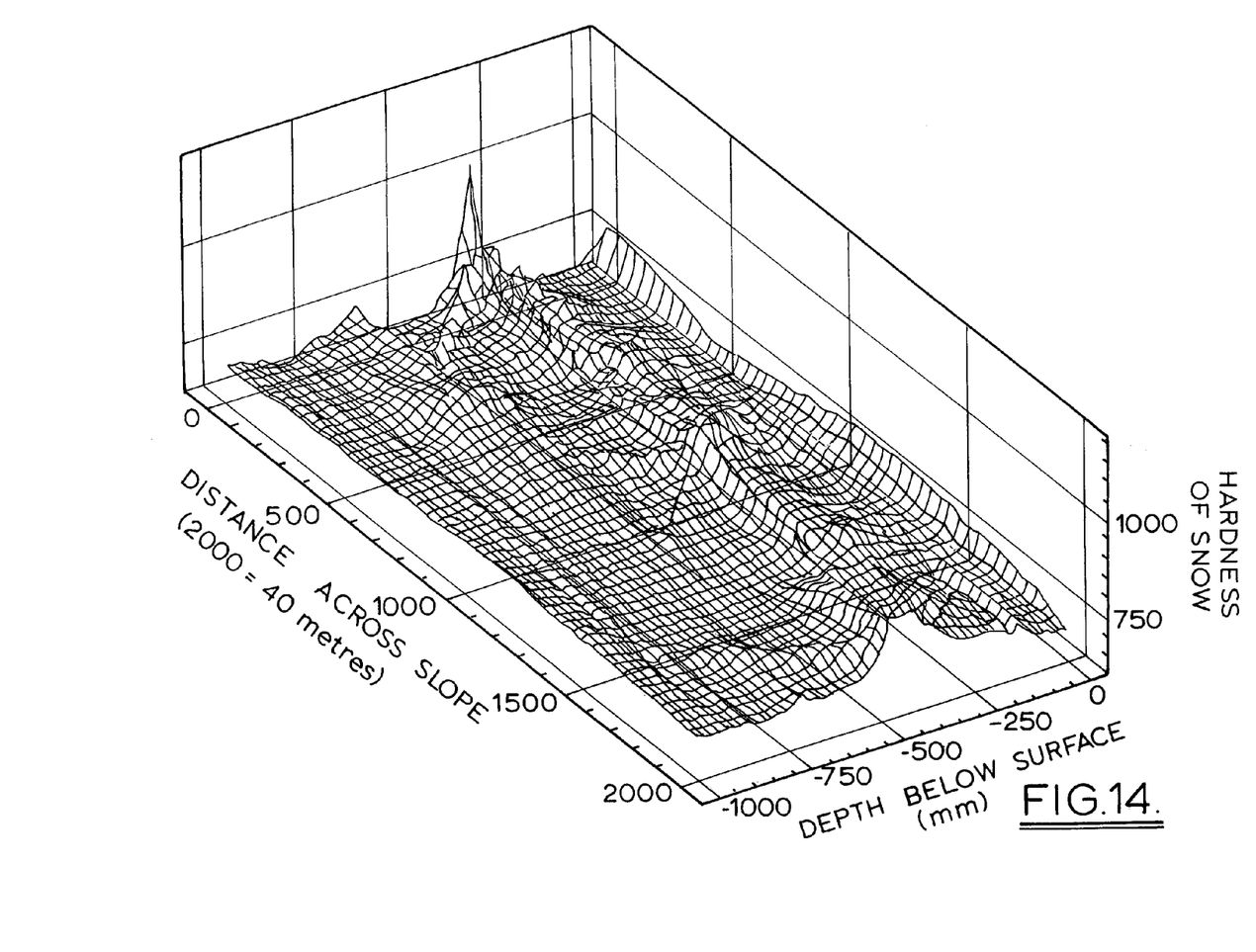

FIG. 11 shows a succession of probe measurements which in FIG. 12 are plotted as depth versus distance across slope with colors indicating the hardness of the snow. In FIGS. 13 and 14 this data is presented on a three axis contour chart.

The controller for the probe contains software to provide a read out of the results of an insertion of the probe. This controller may be a handheld computer.

The following description of the probe operation relates to one particular embodiment of the invention.

As the probe is inserted data is generated from the force probe the accelerometer and the temperature probe and stored into a temporary buffer during the push.

A/d conversion starts immediately and the data is put into the FIFO. When the conversion is stopped the most recent 16.384 s of data are preserved to allow an arbitrary set up time. For analysis the probe is expected to be at rest for 0.5 s at the beginning and end of the data in the FIFO.

The two main data transformations are to analyse the acceleration and analyse the force data.

Acceleration Algorithm

The start and end points are not zero due to low frequency noise in solid state accelerometers. This means that integration to velocity gives values even when the probe is at rest and thus the low frequency noise gives a positional error. To correct for this effect an iterative process is used to straighten the velocity and acceleration to give a zero velocity at rest.

2. straighten acceleration
      get mean of start segment (pause time before push)
      get mean of end segment (pause time before push)
      find slope between start and end (should be zero)
      if not zero then adjust acceleration based based on a non zero slope
  3. straighten velocity
      integrate acceleration to velocity
      get mean of start segment (pause time before push)
      get mean of end segment (pause time before push)
      find slope between start and end (should be zero) ie: zero velocity
      if not zero then adjust acceleration based based on a non zero slope
  4. find new limits
      find the start and end position of scan from the trial velocity adding +/−50 data pointes as a safety margin so as not to cut off non paused data. This subroutine minimizes the effect of the slope adjustment leading to a negative/positive velocity/positional effect at the beginning and end of the scan after the first adjustment.
      Find maximum and minimum of velocity
      Set threshold
      Find start
      Subtract margin
      Find end
      Add margin
  5. Use the new limits
      Repeat steps 1
  6. Integrate new velocity profile to position Analyse Force The algorithm used is analogous to that used by a guide during a snow pit test. Each layer is stored with depth and an additional algorithm is used to determine the appropriate force for that layer. A look up table is used to correlate the force reading to a hand scale used by guides.

The force data is converted from bit data to mV/N using calibration factors. It should be noted that snow may have inertial effects causing strain rate sensitivity. This means that if the speed of the probe is varied the force required will change. Hence based on velocity of the push through each layer a correction factor can be introduced modifying the force to the correct value.

This will not be needed if inertial effects are not observed.

Analysing Force Data for Layer Interpretation, Storage and Display

The initial force data is 8192 readings which is the default size of the FIFO buffer.

Storage

To enable storage of as many scans as possible the data is decimated to 1000 readings 1. divide data into equal length (positions) bins to give 1000 bins
2. find the maximum value in each bin. This becomes the new force value
3. store the new force and positions to flash memory.

Display

The graphics display used in this embodiment has only 128 pixels and hence only 120 points can be displayed
1. divide data into equal length (positions) bins to give 1000 bins
2. find the maximum value in each bin. This becomes the new force value
3. display to graphics screen Layer Interpretation The layer interpretation is based on using a number of logic statements for pattern recognition in the force-position data.

The routine may use a single pass (iteration). Nine possible events are considered to ascertain whether a layer change has occurred, the type of layer and whether the layer is constant or stiffens or softens within the layer. A typical value of force for each layer is designated and correlated to the standard pit test. This gives rise to one of 5 designations.

FIST
HAND
FINGER
PEN
KNIFE

The data is then displayed on the graphics screen as text form
Layer number,
Force in Newton's of each layer,
depth of layer,
Designation of each layer,
slope of each layer as a + increasing
− decreasing
N no change in layer The probe can be manually inserted into the snow and a reading obtained within two minutes. An entire slope can be measured in the time it takes to dig a single snow pit. To obtain a cross slope projection the point data can be processed into a 3 dimensional image using software such as tech plot that provides images such as those in FIGS. 13 and 14.

From the above it can be seen that this invention provides a soil or snow probe that can give point data for the strength/depth measurements which can be taken quickly and which can be processed to give a profile of the layers of a soil area or a snow slope. The absence of subjective interpretation allows the collection of objective quantitative measurements of snow pack strength and enables an assessment to be made of stability.

Although this invention has been described in relation to one embodiment of a snow probe those skilled in the art will realise that the invention is adaptable to being used for any material where a manual insertion to measure properties that are depth related is required such as soil, sand or bogs.

Variations and modifications may be made to adapt this device and method to provide additional sensed data such as temperature or water content in soils.

The invention claimed is:

1. A penetrating probe for testing soil or snow stability which includes
a) a head shaped for penetrating soil or snow;
b) a sensing unit mounted in said head to sense the resistance to penetration which includes a load cell incorporating a low duro polymer that behaves as a non compressible fluid wherein the impact of the head impacting the soil or snow is transferred to the low duro polymer;
c) an accelerometer to sense the acceleration of the head as it moves and derive depth of penetration;
d) a processor able to receive signals from said sensing unit and said accelerometer and programmed to analyze the data and present it as a vertical profile of penetration resistance with depth of penetration.

2. A probe as claimed in claim 1 which includes at least two sensor heads attached to a vertical shaft each sensor head being of a different diameter.

3. A probe as claimed in claim 1 in which the sensing unit senses one or more of the following as a function of depth of penetration
a) resistance to penetration
b) temperature
c) moisture content
d) external pressure.

4. A probe as claimed in claim 1 in which a sensor is in contact with said low duro polymer to provide a measure of the forces transmitted to said low duro polymer.

5. A probe as claimed in claim 4 in which the low duro polymer is a natural or synthetic rubber, a polyurethane or a silicone polymer.

6. A probe as claimed in claim 4 in which the penetrating head is mounted on a shaft which seats on said low duro polymer such that forces acting on said head are transmitted to said low duro polymer by a spherically domed surface.

7. A force sensor which includes:
a) a low duro polymer;
b) an impact head mounted on a shaft which seats on said low duro polymer such that forces acting on said impact head are transmitted to said low duro polymer by a spherically domed surface;
c) a sensor in contact with said low duro polymer to provide a measure of the forces transmitted to said low duro polymer.

8. A method of assessing the stability of a snow slope which includes the steps of:
a) using a probe to produce a profile of resistance to penetration as a function of penetration depth, the probe including a head shaped for penetrating soil or snow, a sensing unit mounted in said head to sense the resistance to penetration which includes a load cell incorporating a low duro polymer that behaves as a non compressible fluid wherein the impact of the head impacting the soil or snow is transferred to the low duro polymer, an accelerometer to sense the acceleration of the head as it moves and derive depth of penetration, a processor able to receive signals from said sensing unit and said accelerometer and programmed to analyze the data and present it as a vertical profile of penetration resistance with depth of penetration;
b) repeating step a) at different points on the slope;
c) integrating the results of step b) to produce a profile of the slope.

9. A method as claimed in claim 8 wherein the points are taken at 10 to 15 meter spacings in line across the contour of a slope.

* * * * *